United States Patent
Bow et al.

(10) Patent No.: US 6,774,261 B2
(45) Date of Patent: Aug. 10, 2004

(54) HIGH PURITY AMINO-ORGANOSULFONIC ACID ZWITTERIONIC COMPOSITIONS

(75) Inventors: David Bow, Mason, OH (US); Glenn Thomas Carroll, Norristown, PA (US)

(73) Assignee: Buffers & Biochemicals Corporation, Loveland, OH (US)

(*) Notice: Subject to any disclaimer, the term of this patent is extended or adjusted under 35 U.S.C. 154(b) by 0 days.

(21) Appl. No.: 10/231,318

(22) Filed: Aug. 29, 2002

(65) Prior Publication Data

US 2004/0044208 A1 Mar. 4, 2004

(51) Int. Cl.[7] .............................................. C07C 309/00
(52) U.S. Cl. ........................ 562/30; 516/198; 516/200; 516/201; 516/203; 516/204
(58) Field of Search ............................ 562/30; 516/198, 516/200, 201, 203, 204

(56) References Cited

U.S. PATENT DOCUMENTS

| | | |
|---|---|---|
| 2,109,401 A | 2/1938 | Nicodemus et al. |
| 4,169,950 A | 10/1979 | Ferguson |
| 4,246,194 A | 1/1981 | Ferguson |
| 4,481,150 A | 11/1984 | Ishii et al. |
| 4,582,651 A | 4/1986 | Ishii et al. |
| 4,657,704 A | 4/1987 | Yamamoto et al. |
| 4,935,373 A | 6/1990 | Christiansen |
| 5,430,052 A | 7/1995 | Higashiura et al. |
| 6,117,831 A | 9/2000 | Chiang et al. |
| 6,124,496 A | 9/2000 | Wu et al. |

OTHER PUBLICATIONS

Ferguson et al, Analytical Biochemistry, (1980), vol. 104, 300–310.*

Thomas J. O'Shea and Susan M. Lunts, "Selective Detection of Free Thiols by Capillary Electrophoresis–Electrochemistry Using a Gold/Mercury Amalgam Microelectrode," Anal. Chem., vol. 65, pp. 247–250, 1993.

Wilfred J. Ferguson et al., "Hydrogen Ion Buffers for Biological Research," Analytical Biochemistry, vol. 104, pp. 300–310, 1980.

Rabrindra N. Roay et al., "Standard Buffer of N,N–Bis(2–Hydroxyethyl)–2–Aminoethanesulfonic Acid (Bes) for Use in the Physiological pH Range 6.6 to 7.4," Anal. Chem., vol. 47, No. 8, pp. 1407–1410, Jul. 1975.

Norman E. Good et al., "Hydrogen Ion Buffers for Biological Research," Biochemistry, vol. 5, No. 2, pp. 467–477, Feb. 1966.

C.F.H. Allen et al., "Sultones as Reagents for Derivatizing Aliphatic Amines in Qualitative Organic Analysis," Anal. Chem., vol. 37, No. 1, pp. 156–158, Jan. 1965.

* cited by examiner

Primary Examiner—Paul J. Killos
Assistant Examiner—Hector M. Reyes

(57) ABSTRACT

This invention relates to high purity hydrogen ion buffers and in particular amino-organosulfonic acid zwitterionic compositions having low metal content. The concentration of any single metal in the composition is no greater than about 500 ppb, and ideally is less than about 20 ppb.

19 Claims, No Drawings

HIGH PURITY AMINO-ORGANOSULFONIC ACID ZWITTERIONIC COMPOSITIONS

TECHNICAL FIELD

This invention relates to high purity hydrogen ion buffers. More particularly, this invention relates to amino-organosulfonic acid zwitterionic compositions having low metal content which are particularly desirable for use in the electronics industry.

BACKGROUND OF INVENTION

A group of hydrogen ion buffers has been discussed by Good et al., in *Biochemistry*, Volume 5, No. 2, pages 467–477, 1966. Some of these buffers may be generally classified as substituted amino-organosulfonic acid zwitterions. These materials have a variety of uses including pH control in printing inks, bioprocessing and electronic component manufacture. However, in the electronics industry, the materials used must have at most, very low levels of impurities, such as metals ranging from alkali to silicon whose presence may increase the propensity of component failure. There continues to be a need for high purity amino-organosulfonic acid zwitterionic buffers with very low metal concentrations for use in the electronics industry.

SUMMARY OF INVENTION

The present invention comprises an amino-organosulfonic acid zwitterionic composition comprised of an amino-organosulfonic acid zwitterion having the general structure:

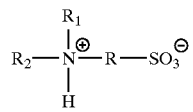

wherein $R_1$ and $R_2$ are each independently a hydrogen atom, an aliphatic, cycloaliphatic, substituted aliphatic, substituted cycloaliphatic, aryl, substituted aryl, heterocyclic group or substituted heterocyclic group, or $R_1$ and $R_2$ are joined to form a cycloaliphatic, substituted cycloaliphatic, aryl, substituted aryl, heterocyclic group or substituted heterocyclic group, wherein $R_1$ and $R_2$ preferably range from $C_1$ to $C_{20}$ and more preferably from $C_1$ to $C_{10}$, or together form a substituted heterocyclic group. more preferred is a substituted piperazine such as 2-hydroxyethylpiperazine; and R is an aliphatic, cycloaliphatic, hydroxyaliphatic, or an aryl group ranging from $C_1$ to $C_{20}$ and preferably aliphatic ranging from $C_2$ to $C_4$; and wherein the concentration of any single metal in the composition is no greater than about 500 ppb, and preferably is less than about 200 ppb, more preferably is less than about 150 ppb, even more preferably is less than about 100 ppb, most preferably is less than about 50 ppb, and ideally is less than about 20 ppb. These metals are selected from the group consisting of aluminum, antimony, barium, boron, cadmium, calcium, chromium, cobalt, copper, gallium, germanium, gold, iron, lead, magnesium, manganese, nickel, potassium, silicon, silver, sodium, strontium, tantalum, tin, and titanium and mixtures thereof. Each of the metals may be present individually, or any combination thereof. There is no total metal concentration requirement, but each metal present must be present at no greater concentration than about 500 ppb.

Examples of amino-organosulfonic acid zwitterions include, but are not limited to 4-(2-Hydroxyethyl) piperazine-1-ethanesulfonic acid, 4-Morpholinepropanesulfonic acid, b-hydroxy-4-morpholinepropanesulfonic acid, 2-(N-Morpholino)-ethanesulfonic acid, 1,4-piperazinebis(ethanesulfonic acid), N,N-Bis(2-hydroxyethyl)-2-aminoethanesulfonic acid, 2-[(2-Hydroxy-1,1-bis[hydroxymethyl]ethyl)-aminoethane-sulfonic acid, and 2-(Cyclohexylamino)ethanesulfonic acid.

The present invention also relates to a method of producing a composition which comprises an amino-organosulfonic acid zwitterion and wherein the concentration of any single metal in the composition has a concentration no greater than about 500 ppb, preferably less than 200 ppb, more preferably less than about 150 ppb and even more preferably, less than about 100 ppb, most preferably less than about 50 ppb and ideally less than about 20 ppb. The method for achieving low metal concentrations consists of the following steps: (i) dissolving the amino alkyl sulfonate in an aqueous solution; (ii) flowing the aqueous solution through an iminodiacetic ion-exchange resin; (iii) flowing the aqueous solution through an electrodialysis apparatus comprised of a two-compartment cell configuration having anion and cation exchange membranes; (iv) flowing the aqueous solution through a basic ion-exchange resin wherein the basic ion-exchange resin has a pH of at least 9; (v) flowing the aqueous solution through a mixed bed ion-exchange resin; and (vi) filtering the aqueous solution through a filter having a pore size of about 0.5 microns to about 0.2 microns and is preferably about 1 micron. The order of these steps (ii)–(v) is not critical and they may be carried out in any sequence. The amount of de-ionized water the sample may be dissolved in varies from a concentration of from about 9:1 to about 1:9, by weight (sulfonic acid: water).

DETAILED DESCRIPTION OF INVENTION

The present invention provides a composition comprising amino-organosulfonic acid zwitterions (herein also referred to as "sulfonic acids") having low metal content, wherein the concentration of any single metal in the composition is no greater than about 1 ppm. The metals are selected from the group consisting of aluminum, antimony, barium, boron, cadmium, calcium, chromium, cobalt, copper, gallium, germanium, gold, iron, lead, magnesium, manganese, nickel, potassium, silicon, silver, sodium, strontium, tantalum, tin, and titanium and mixtures thereof. The present invention also provides for a method of forming such compositions.

The amino-organosulfonic acid zwitterionic compounds of the present invention have the following general formula:

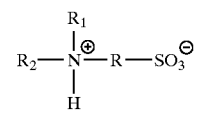

wherein $R_1$ and $R_2$ are each independently a hydrogen atom, an aliphatic, cycloaliphatic, substituted aliphatic, substituted cycloaliphatic, aryl, substituted aryl, heterocyclic group or substituted heterocyclic group, or $R_1$ and $R_2$ are joined to form a cycloaliphatic, substituted cycloaliphatic, aryl, substituted aryl, heterocyclic group or substituted heterocyclic group, wherein $R_1$ and $R_2$ preferably range from $C_1$ to $C_{20}$ and more preferably from $C_1$ to $C_{10}$, or together form a substituted heterocyclic group. more preferred is a substituted piperazine such as 2-hydroxyethylpiperazine; and R is an aliphatic, cycloaliphatic, hydroxyaliphatic, or an aryl group ranging from $C_1$ to $C_{20}$ and preferably aliphatic ranging from $C_2$ to $C_4$.

These amino-organosulfonic acid zwitterionic compounds are available commercially or may be produced by methods known to those skilled in the art. Such methods are disclosed in U.S. Pat. No. 2,109,401, Nicodemus et al, issued Oct. 23, 1935; U.S. Pat. No. 4,169,950, Ferguson, issued Oct., 2, 1979; U.S. Pat. No. 4,246,194, Ferguson, issued Jan. 20, 1981; U.S. Pat. No. 4,657,704, Yamamoto et al, issued Apr. 14, 1987; U.S. Pat. No. 4,953,373, Christiansen, issued Jun. 19, 1990; U.S. Pat. No. 5,430,052, Higashiura et al, issued Jul. 4, 1995; Good et al., *Biochemistry*, vol. 5, pages 467–477, 1966; C. F. H. Allen et al., *Anal. Chem.* Vol. 37, page 156, 1965; *Anal. Chem.* vol. 65, page 247, 1993; A. Champseix et al., *Bull. Chem. Soc. France*, page 463, 1965; *Anal. Biochem.* vol. 104, page 300, 1980; *Anal. Chem.* vol. 47, no. 8, pages 1407–1410, 1975; all of which are herein incorporated by reference.

Generally, the method for producing the amino-organosulfonic acid zwitterionic compositions with low metal content, comprises the following steps: (i) passing an aqueous solution of the amino-organosulfonic acid zwitterion through an iminodiacetic acid (IDA) resin, such as DOWEX IDA-1™; (ii) treating the aqueous composition by electrodialysis for removal of cationic and anionic impurities; (iii) passing the aqueous solution through a strong base anion exchange resin; (iv) passing the aqueous solution through a mixed-bed ion-exchange resin; and (v) ultra-filtration of the aqueous solution. The order of these steps (ii)–(v) is not critical and they may be carried out in any sequence. The details of this procedure are described below.

Prior to purification, the sulfonic acid is initially dissolved in deionized water, in a concentration, by weight, ranging from about 9:1 to about 1:9, by weight (sulfonic acid:water), and is stirred until dissolved.

In order to initially remove any metals from the sulfonic acid, the aqueous solution of the sulfonic acid is passed through an iminodiacetic acid resin at temperatures ranging from about 20° C. to about 55° C., preferably from about 20° C. to about 45° C., and more preferably from about 20° C. to about 35° C. The preferred iminodiacetic acid resin is DOWEX IDA-1™. The resin is generally loaded onto a column by methods known to those skilled in the art of ion-exchange fluid dynamics. The solution containing the sulfonic acid is flowed through the column at a rate specified by the resin manufacturer and is known to those skilled in the art. There is no end-point determination. Rather, completion is based on resin capacity. Once the solution has passed through the column, ultra-filtered, sterile, de-ionized water is passed through the column to remove any remaining sulfonic acid located in the void volume of the resin.

After this initial metals removal process, the solution is then transferred to an electrodialysis system having a two-compartment cell configuration with anion and cation exchange membranes. Most standard membranes should work for the removal of cationic and anionic impurities. To establish the endpoints, the same data is used to calculate the filter or resin capacity.

Subsequent to the electrodialysis step to further remove trace impurities the aqueous solution containing the sulfonic acid is then passed through a macroporous strong base ion-exchange resin. The pH of the basic resin is at least about 8. The resin is generally loaded onto a column by methods known to those skilled in the art of ion-exchange fluid dynamics. The solution containing the sulfonic acid is flowed through the column at a rate specified by the resin manufacturer. Once the solution has passed through the column, ultra-filtered, UV sterilized, de-ionized water is flowed through the column to remove any residual sulfonic acid located in the void volume of the resin. There is no endpoint determination for this step. Rather, the completion of this step is based on resin capacity and metals testing by analyzing for the presence of metal ions in the solution.

Following treatment with the strongly basic ion-exchange resin, the solution is passed through a mixed-bed ion-exchange resin. The resin is generally loaded onto a column by methods known to those skilled in the art of ion-exchange fluid dynamics. The solution containing the sulfonic acid is flowed through the column at a rate specified by the resin the manufacturer. Once the solution is flowed through the column, ultra filtered, UV sterilized, de-ionized water is flowed the column to remove any residual sulfonic acid located in the void volume of the resin.

In the final step, the solution is filtered using a filtration system with a pore size ranging from about 0.1 micron to about 0.2 micron. Flow rates are based on the scale of the experiment and the designed flow rates form the various resins, media or electrodialysis systems.

The following example is illustrative of the present invention.

EXAMPLE

An aqueous solution containing 45% of an amino-organosulfonic acid zwitterion (by weight) is prepared from the commercially available compound (see Table 1 for initial metal content of the solution). The solution (at a pH of about 10) is passed through a cation exchange resin to provide a solution with a pH of from about 7.25 to about 7.5. This solution is subsequently passed through an iminodiacetic acid resin exchange resin at 25° C. to further reduce the sodium content. The solution is subsequently passed through an electrodialysis system having a two-compartment cell configuration with anion and cation membranes. The solution is next passed through a strongly basic anion exchange resin, followed by a mixed bed ion-exchange column. The solution is then filtered through a 0.2-micron filter to produce a high purity sulfonic acid with low metal content (see Table 1). Flow rates are based on the scale of the experiment and the designated flow rates are determined form the various resins, media or electrodialysis systems and are commonly known to those skilled in the art.

TABLE 1

Metal content (by ICP analysis) in amino-organosulfonic acid zwitterion after purification.

| Metal | Metal concentration prior to purification (ppm) | Metal concentration after to purification (ppb) | Detection limit (DL) (ppb) |
| --- | --- | --- | --- |
| Al | 0.12 | 10 | 6 |
| Ba | 0.47 | <DL* | 0.07 |
| Ca | 2.0 | 8 | 1 |
| Cr | 0.05 | <DL* | 0.3 |
| Cu | 0.14 | <DL* | 3 |
| Fe | 24 | 10 | 0.7 |
| K | 0.3 | <DL* | 6 |
| Mg | 0.04 | 5 | 0.05 |
| Mn | 0.004 | <DL* | 0.1 |
| Na | >>10,000 | 7 | 0.5 |
| Si | 4.5 | 20 | 7 |
| Ti | 0.7 | <DL* | 1 |

TABLE 1-continued

Metal content (by ICP analysis) in amino-organosulfonic acid zwitterion after purification.

| Metal | Metal concentration prior to purification (ppm) | Metal concentration after to purification (ppb) | Detection limit (DL) (ppb) |
|---|---|---|---|

DL = detection limit;
ICP is the standard test to measure the individual metals at low levels.

What is claimed is:

1. An amino-organosulfonic acid zwitterionic composition comprised of an amino-organosulfonic acid zwitterion, wherein the concentration of any single metal in said composition is no greater than about 500 ppb.

2. The amino-organic sulfonic acid zwitterionic composition of claim 1, wherein the amino-organicsulfonic acid zwitterion has the general structure:

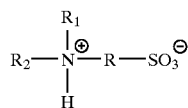

and wherein $R_1$ and $R_2$ are each independently a hydrogen atom, an aliphatic, cycloaliphatic, substituted aliphatic, substituted cycloaliphatic, aryl, substituted aryl, heterocyclic group or substituted heterocyclic group, or $R_1$ and $R_2$ are joined to form a cycloaliphatic, substituted cycloaliphatic, aryl, substituted aryl, heterocyclic group or substituted heterocyclic group, wherein $R_1$ and $R_2$ range from $C_1$ to $C_{20}$, or together form a substituted heterocyclic group and R is an aliphatic, cycloaliphatic, hydroxyaliphatic, or an aryl group ranging from $C_1$ to $C_{20}$.

3. The composition of claim 2 wherein $R_1$ and $R_2$ together form a substituted piperazine.

4. The composition of claim 2 wherein the metal is selected from the group consisting of aluminum, antimony, barium, boron, cadmium, calcium, chromium, cobalt, copper, gallium, germanium, gold, iron, lead, magnesium, manganese, nickel, potassium, silicon, silver, sodium, strontium, tantalum, tin, and titanium and mixtures thereof.

5. The composition of claim 4 wherein the concentration of each metal is less than about 200 ppb.

6. The composition of claim 4 wherein the concentration of each metal is less than about 150 ppb.

7. The composition of claim 4 wherein the concentration of each metal is less than about 100 ppb.

8. The composition of claim 4 wherein the concentration of each metal is less than about 50 ppb.

9. The composition of claim 4 wherein the concentration of each metal is less than about 20 ppb.

10. The composition of claim 1 wherein the amino-organosulfonic acid zwitterionic compositions is selected from the group of amino-organosulfonic acids consisting of but not limited to: 4-(2-hdroxyethyl)piperazine-1-ethanesulfonic acid, 4-morpholinepropanesulfonic acid, b-hydroxy-4-morpholinepropanesulfonic acid, 2-(N-Morpholino)ethanesulfonic acid, 1,4-piperazinebis (ethanesulfonic acid), N,N-Bis(2-hydroxyethyl)-2-aminoethanesulfonic acid, 2-[(2-Hydroxy-1,1-bis[hydroxymethyl]ethyl)amino]ethanesulfonic acid, and 2-(Cyclohexylamino)ethanesulfonic acid.

11. The composition of claim 1 wherein the amino alkyl sulfonic acid zwitterion is 4-(2-Hydroxyethyl)piperazine-1-ethanesulfonic acid.

12. The composition of claim 9 wherein the amino alkyl sulfonic acid zwitterion is 4-(2-Hydroxyethyl)piperazine-1-ethanesulfonic acid.

13. The composition of claim 2 wherein $R_1$ and $R_2$ range from $C_1$ to $C_{10}$, and wherein R ranges from $C_2$ to $C_4$.

14. A method of producing a composition which comprises an amino-organosulfonic acid zwitterion and wherein the concentration of any single metal in said composition has a concentration of less than about 1 ppm, said method comprising the steps of:
    a) dissolving the amino-organosulfonic acid zwitterion in an aqueous solution;
    b) flowing the aqueous solution of step (a) through an ion-exchange resin;
    c) flowing the aqueous solution of step (b) through an electrodialysis apparatus;
    d) flowing the aqueous solution through a basic ion-exchange resin;
    e) flowing the aqueous solution through a mixed bed ion-exchange resin; and
    f) filtering the aqueous solution through a filter having a pore size of about 0.5 microns to about 0.2 microns.

15. The method of claim 14 wherein the amino-organosulfonic acid is dissolved in de-ionized water at a concentration of from about 9:1 to about 1:9, by weight, sulfonic acid:water.

16. The method of claim 14 wherein the ion-exchange resin of step (b) is an iminodiacetic acid resin.

17. The method of claim 14 wherein the electrodialysis apparatus of step (c) is comprised of a two-compartment cell configuration having anion and cation exchange membranes.

18. The method of claim 14 wherein the basic ion-exchange resin of step (d) has a pH of at least about 9.

19. The method of claim 14 wherein the filter pore size of step (f) is about 1 micron.

* * * * *